United States Patent [19]
Hoornaert et al.

[11] Patent Number: 5,434,903
[45] Date of Patent: Jul. 18, 1995

[54] X-RAY EXAMINATION APPARATUS COMPRISING ADJUSTMENT-CONTROL MEANS AND ADJUSTMENT-CONTROL MEANS FOR USE IN AN X-RAY EXAMINATION APPARATUS

[75] Inventors: Bart P. A. J. Hoornaert; Jacques O. Hoorn, both of Eindhoven, Netherlands

[73] Assignee: U.S. Philips Corporation, New York, N.Y.

[21] Appl. No.: 150,527

[22] Filed: Nov. 10, 1993

[30] Foreign Application Priority Data

Nov. 10, 1992 [EP] European Pat. Off. ........... 92203436

[51] Int. Cl.6 .............................................. A61B 6/00
[52] U.S. Cl. ..................... 378/116; 378/101; 378/98
[58] Field of Search ............. 378/116, 20, 98, 98.12, 378/108, 110, 112, 114, 147, 150, 205

[56] References Cited

U.S. PATENT DOCUMENTS

| | | | |
|---|---|---|---|
| 4,277,685 | 7/1981 | Covic et al. | 378/150 X |
| 4,329,590 | 5/1982 | Adelmeyer | 378/151 X |
| 4,928,283 | 5/1990 | Gordon | 378/20 |
| 5,103,469 | 4/1992 | Tanaka | 378/205 X |
| 5,155,757 | 10/1992 | Sakaniwa et al. | 378/197 |

FOREIGN PATENT DOCUMENTS 0220501  5/1987  European Pat. Off. .
1085636  9/1987  Japan .

*Primary Examiner*—David P. Porta
*Attorney, Agent, or Firm*—Jack D. Slobod

[57] ABSTRACT

X-ray examination apparatus comprising adjustment-control means and adjustment-control means for use in an X-ray examination apparatus.

An X-ray examination apparatus is provided with adjustment-control means suitable for retrieving the orientation of the X-ray beam and of the X-ray beam optics as were employed for making a reference image. Thus the X-ray examination apparatus can be automatically and accurately placed in the same imaging conditions in which a previous image was made.

9 Claims, 1 Drawing Sheet

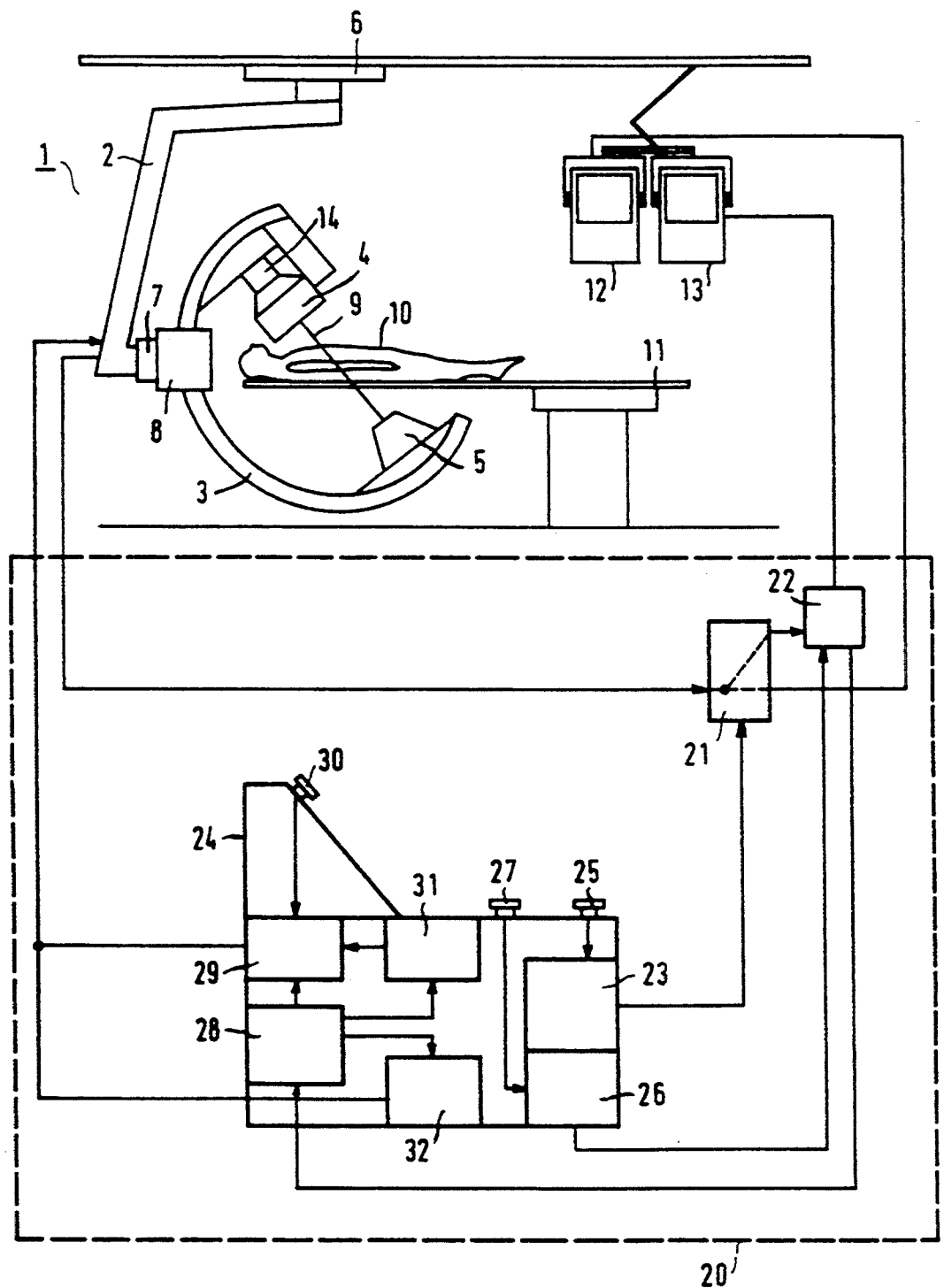

X-RAY EXAMINATION APPARATUS COMPRISING ADJUSTMENT-CONTROL MEANS AND ADJUSTMENT-CONTROL MEANS FOR USE IN AN X-RAY EXAMINATION APPARATUS

BACKGROUND OF THE INVENTION

1. Field of the Invention

The invention pertains to an X-ray examination apparatus including an X-ray source for generating an X-ray beam, an X-ray detector facing the X-ray source for recording an X-ray image, and an adjustment-control means incorporating a memory for storing values of imaging parameters. The invention also relates to an adjustment-control for use in such an X-ray examination apparatus.

2. Description of the Related Art

An X-ray examination apparatus of said kind has been described in the European Patent EP 0 220 501.

An X-ray examination apparatus as described in the cited reference comprises an adjustment-control means incorporating a memory-means for storing values of imaging parameters, in particular a preset sequence of positions of the X-ray stand corresponding to a sequence of X-ray exposures. Each of the exposures pertains to imaging an object, notably a patient, employing a different angle of irradiation of the object.

SUMMARY OF THE INVENTION

It is inter alia an object of the invention to provide an X-ray examination apparatus having an arrangement for automatically achieving a selected imaging adjustment.

To achieve this an X-ray examination apparatus in accordance with the invention is characterised in that the adjustment-control means comprises an image-specification-means to specify an image as a reference image, a memory means arranged to store said reference image together with exposure information concerning imaging adjustment pertaining to said stored reference image, an image-selection means to retrieve a stored reference image together with exposure information belonging to a retrieved reference image, and image-control means for controlling imaging adjustments to be in correspondence with said exposure information.

Rather than identifying positions of the X-my stand and adjustments of beam optics by storing numerical data, selecting imaging parameters is performed by identifying imaging parameters by means of identifying imaging parameters by an image made previously. An image can be selected as a reference image, which is subsequently stored together with imaging adjustment parameters belonging to said reference image. Because imaging adjustment parameters of the X-my examination apparatus are stored together with an image, an adjustment of the X-ray examination apparatus pertaining to the image made previously is readily retrieved.

A preferred embodiment of an X-my examination apparatus in accordance with the invention, and said stand being moveable, is characterised in that said exposure information comprises a position of the moveable stand corresponding to a beam path orientation pertaining to said stored reference image, and in that the adjustment-control means comprises motion-control means for controlling the stand to be in a position in correspondence with said retrieved exposure information.

For imaging an object by the same beam path orientation as was employed for making the stored image, the current position of the X-ray stand is compared to a target position stored in said memory means together with the reference image. Should the current position of the X-ray stand differ from the target position of the X-ray stand, then the X-ray stand is moved from the current position to the target position of the X-ray stand.

A further preferred embodiment of an X-ray examination apparatus in accordance with the invention is characterised in that said exposure information comprises beam optics adjustments pertaining to said stored reference image and in that the adjustment-control means comprises a beam-optics-control means for controlling beam optics adjustment to be in correspondence with said exposure information.

For imaging an object by the same beam optics adjustment as was employed for making the stored image, the current beam optics adjustment of the X-ray stand is compared to a target beam optics adjustment stored in said memory means together with the reference image. Should the current beam optics adjustment differ from the target position, then the beam optics adjustments are changed from the current beam optics adjustment to the target beam optics adjustment. These adjustments are made by positioning beam shutters and wedge filters being incorporated in the X-ray source into required positions.

A further preferred embodiment of an X-my examination apparatus in accordance with the invention comprising also a moveable patient support table, is characterised in that said exposure information comprises a patient support table position pertaining to said stored reference image and in that the adjustment-control means comprises motion-control means for controlling the patient support table to be in a position in correspondence with said exposure information.

For imaging a same part of an object as was performed for making the stored image, the current position of the patient support table is compared to a target position stored in said memory means together with the reference image. Should the current position of the patient support table differ from the target position of the patient support table, then the patient support table is moved from the current position to the target position of the patient support table.

An adjustment-control means suitable for use in an X-my examination apparatus in accordance with the invention preferably comprises an image-specification-means for specifying an image as a reference image, a memory means arranged for storing said reference image together with values of imaging parameters concerning imaging adjustment pertaining to said stored reference image, an image-selection means to retrieve a stored reference image together with retrieved values of imaging parameters belonging to a retrieved reference image and image-control means for controlling imaging adjustments to be in correspondence with said retrieved values of imaging parameters.

These and other aspects of the invention will become apparent from and elucidated with reference to the embodiments described hereinafter and with reference to the accompanying drawing.

BRIEF DESCRIPTION OF THE DRAWING

A schematic view of an X-ray examination apparatus in accordance with the invention is presented in the sole Figure of the accompanying drawing.

DETAILED DESCRIPTION OF THE PREFERRED EMBODIMENT

The sole Figure shows a schematic view of an X-ray examination apparatus in accordance with the invention. An X-ray stand 1 comprising a support 2 being suspended from the ceiling of a room wherein the X-ray examination apparatus is placed and a C-shaped carrier 3 being mounted to the support 2. An X-ray detector 4, notably an X-ray image intensifier and an X-ray source 5 are mounted to the C-shaped carrier. By means of a first bearing 6, the support 2 is rotatable and by means of a second bearing 7 the C-shaped carrier is rotatable with respect to the support 2. The C-shaped carrier is mounted to the support 2 by means of a sleeve 8 and the C-shaped carrier 3 is moveable through the sleeve 8. Therefore a the central beam path 9 can be oriented in different directions for imaging portions of the body of a patient 10 by making projections from different angles. In particular for coronary investigations a number of projections from various angles are preferably made to obtain sufficient information for adequately reaching a diagnosis. The patient 10 is positioned on a table 11 which is moveable so as to position a relevant part of the body of an patient for irradiation by the X-ray source. Images can be viewed from a first monitor 12 or from a second monitor 13. An adjustment-control-means 20 is provided for controlling various imaging parameters. Such imaging parameters contain exposure information, such as imaging angles, in particular positions of the C-shaped carrier 3, the support 2 and the image intensifier 4 must be selected for performing a required X-ray exposure. In addition, there are imaging adjustments to be made concerning beam optics by means of e.g. a radiation diaphragm and wedge filters being incorporated in the X-ray source 5.

By means of an image sensor 14 being incorporated in the X-ray detector, an X-ray image produced by the X-ray detector 4 is converted into an electronic image signal. The electronic image signal is supplied to a switching-means 21 and is selectively supplied to an image-memory 22 or directly to the first monitor 12. The switching-means 21 is controlled by an image-specification-means 23 incorporated in a control desk 24. By operating a control-button 25 the image specification-means 23 activates the switching-means 21 so as to store an image in the image-memory 22 as a reference image. Together with the electronic image signal, corresponding imaging parameters are stored in the image-memory 22 together with the image. Often, during an X-ray examination procedure a first series of exposures from different angles are made; this yields a series of X-ray images which will be referred to as reference images hereinafter. These reference images are stored in the image-memory 22. In a further stage of the treatment of the patient the X-ray examination apparatus is required to be positioned such that the beam path has the orientation in which the reference image was made. For instance, during an interventional procedure, e.g. a catheterisation of a heart, coronary vessels are required to be imaged from the same orientation in which they were imaged on the reference image. Furthermore, in order to ascertain the result of an interventional procedure, an image made after the intervention is to be compared to a corresponding image made before the intervention. An image from the series of reference images can be selected as the current reference image from the control desk 24 by way of an image-selection-means 26 which is incorporated in the control-desk 24 and which is activated by a control-button 27. The selected reference image is supplied from the image memory to the second monitor 13 for viewing. To position the X-ray stand in the position in which the reference image was made, imaging parameters of the current reference image are retrieved from the image-memory 22 and supplied to an imaging-control-means 28, which generates a signal for moving the C-shaped carrier and the support into a required target position and adjusting beam optics. The imaging-control-means 28 is arranged such that when the current orientation of the beam path is within narrow limits (e.g. 2°) of the target orientation of the beam path supplied from the image memory upon activating motion-control-means 29 by way of a control-button 30 no movements are performed and a warning signal is supplied by the imaging-control-means. If the target orientation differs more that said narrow limits from the current orientation, then a computing-means 31 calculates an optimum path for the C-shaped carrier 3, the support 2 and the image intensifier 4 to be moved along to the required target position.

Adjustments pertaining to beam optics, i.e. positions of e.g. beam shutters and wedge filters are aim stored in the image-memory together with a reference image. Similarly to adjusting the position of the X-ray stand and of the patient support table, current adjustments of beam optics are compared to target adjustments of beam optics pertaining to the reference image and beam optics adjustments are changed to said target adjustments by a beam-optics-control-means 32. Adjusting the beam optics is carried out by adjusting beam shutters and wedge filters corresponding to the target beam optics adjustments.

We claim:

1. An X-ray examination apparatus comprising a stand carrying an X-ray source for generating an X-ray beam, an X-ray detector facing the X-ray source for recording an X-ray image, and adjustment-control means comprising an image-specification-means to specify an X-ray image previously obtained by said X-ray examination apparatus as a reference image, a memory means arranged to store said reference image together with exposure information concerning imaging adjustment with which said stored reference image had been obtained, an image-selection means to retrieve a stored reference image together with exposure information belonging to a retrieved reference image and image-control means for controlling imaging adjustments to be in correspondence with said exposure information.

2. An X-ray examination apparatus as claimed in claim 1, said stand being moveable, further characterised in that said exposure information comprises a position of the moveable stand corresponding to a beam path orientation pertaining to said stored reference image, and in that the adjustment-control means comprises motion-control means for controlling the stand to be in a position in correspondence with said retrieved exposure information.

3. An X-ray examination apparatus as claimed in claim 1, further characterised in that said exposure information comprises beam optics adjustments pertaining to said stored reference image and in that the adjustment-control means comprises a beam-optics-control means for controlling beam optics adjustment to be in correspondence with said exposure information.

4. An X-ray examination apparatus as claimed in claim 1, comprising also a moveable patient support table, further characterised in that said exposure information comprises a patient support table position pertaining to said stored reference image and in that the adjustment-control means comprises motion-control means for controlling the patient support table to be in a position in correspondence with said exposure information.

5. An adjustment-control means for use in an X-ray examination apparatus, the adjustment-control means comprising an image-specification-means to specify an X-ray image previously obtained by said X-ray examination apparatus as a reference image, a memory means arranged for storing said reference image together with values of imaging parameters concerning imaging adjustment with which said stored reference image had been obtained, an image-selection means to retrieve a stored reference image together with retrieved values of imaging parameters belonging to a retrieved reference image and image-control means for controlling imaging adjustments to be in correspondence with said retrieved values of imaging parameters.

6. An X-ray examination apparatus as claimed in any one of claim 2, further characterised in that said exposure information comprises beam optics adjustments pertaining to said stored reference image and in that the adjustment-control means comprises a beam-optics-control means for controlling beam optics adjustment to be in correspondence with said exposure information.

7. An X-ray examination apparatus as claimed in claim 2, comprising also a moveable patient support table, further characterised in that said exposure information comprises a patient support table position pertaining to said stored reference image and in that the adjustment-control means comprises motion-control means for controlling the patient support table to be in a position in correspondence with said exposure information.

8. An X-ray examination apparatus as claimed in claim 3, comprising also a moveable patient support table, further characterised in that said exposure information comprises a patient support table position pertaining to said stored reference image and in that the adjustment-control means comprises motion-control means for controlling the patient support table to be in a position in correspondence with said exposure information.

9. An X-ray examination apparatus as claimed in claim 6, comprising also a moveable patient support table, further characterised in that said exposure information comprises a patient support table position pertaining to said stored reference image and in that the adjustment-control means comprises motion-control means for controlling the patient support table to be in a position in correspondence with said exposure information.

* * * * *